(12) United States Patent
Janscha et al.

(10) Patent No.: US 11,067,556 B1
(45) Date of Patent: Jul. 20, 2021

(54) CARBON MONOXIDE SENSOR FOR PORTABLE GENERATOR

(71) Applicant: Briggs & Stratton, LLC, Wauwatosa, WI (US)

(72) Inventors: Ryan Janscha, Brookfield, WI (US); Austin Baeten, De Pere, WI (US)

(73) Assignee: Briggs & Stratton, LLC, Wauwatosa, WI (US)

( * ) Notice: Subject to any disclaimer, the term of this patent is extended or adjusted under 35 U.S.C. 154(b) by 135 days.

(21) Appl. No.: 15/991,327

(22) Filed: May 29, 2018

Related U.S. Application Data

(60) Provisional application No. 62/512,623, filed on May 30, 2017.

(51) Int. Cl.
| | | |
|---|---|---|
| *F02B 77/08* | (2006.01) | |
| *G01N 33/00* | (2006.01) | |
| *F02D 29/06* | (2006.01) | |
| *F02D 41/04* | (2006.01) | |

(52) U.S. Cl.
CPC ......... *G01N 33/004* (2013.01); *F02D 29/06* (2013.01); *F02D 41/042* (2013.01); *G01N 33/0063* (2013.01)

(58) Field of Classification Search
CPC ........ G01N 33/004; F02D 17/02; F02D 41/22
USPC ...................................................... 123/198 D
See application file for complete search history.

(56) References Cited

U.S. PATENT DOCUMENTS

| | | | |
|---|---|---|---|
| 3,703,162 A | 11/1972 | Aono | |
| 5,049,861 A | 9/1991 | Grace et al. | |
| 5,576,739 A | 11/1996 | Murphy | |
| 5,793,296 A | 8/1998 | Lewkowicz | |
| 6,222,349 B1 | 4/2001 | Lerow et al. | |
| 6,433,696 B1 * | 8/2002 | Deiterman | G01N 33/004 340/632 |

(Continued)

FOREIGN PATENT DOCUMENTS

WO   WO-2018/035434 A1   2/2018

OTHER PUBLICATIONS

"Smoke Detector is Beeping Chirping Every 30 Seconds?—How to Reset?," retrieved from https://removeandreplace.com/2015/09/09/smoke-alarm-beeping-chirping-every-30-seconds-how-to-reset> (May 29, 2009).

(Continued)

*Primary Examiner* — Long T Tran
*Assistant Examiner* — James J Kim
(74) *Attorney, Agent, or Firm* — Foley & Lardner LLP

(57) ABSTRACT

A generator includes an internal combustion engine and a carbon monoxide (CO) sensor unit. The CO sensor unit includes a CO sensor controller including a CO sensing circuit configured to detect a level of CO and a shutdown circuit. The shutdown circuit is configured to receive a detected level of CO and calculate a trailing window average of the detected level of CO. The trailing window average includes an average of the detected level of CO over a predetermined sampling window. The shutdown circuit is further configured to determine whether to initiate a shutdown of the generator based on at least the calculated trailing window average and a predetermined trailing window average threshold and initiate the shutdown of the generator based on determining that the trailing window average exceeds the predetermined trailing window average threshold.

22 Claims, 9 Drawing Sheets

(56) References Cited

U.S. PATENT DOCUMENTS

| | | |
|---|---|---|
| 6,983,726 B1 | 1/2006 | Luo et al. |
| 8,286,603 B2 | 10/2012 | Sid |
| 8,375,913 B2 | 2/2013 | Kwiecinski et al. |
| 8,413,642 B2 | 4/2013 | Johnson et al. |
| 8,534,258 B2 | 9/2013 | Cristoforo |
| 8,939,134 B2 | 1/2015 | Sato et al. |
| 9,058,739 B2 | 6/2015 | Sid |
| 9,175,601 B2 | 11/2015 | Markoski |
| 9,293,914 B2 | 3/2016 | Mauk et al. |
| 10,319,207 B1 * | 6/2019 | Janscha .................... G08B 3/00 |
| 2003/0091430 A1 | 5/2003 | Mulera et al. |
| 2007/0085692 A1 * | 4/2007 | Grant ..................... G08B 21/14 |
| | | 340/632 |
| 2008/0015794 A1 | 1/2008 | Eiler et al. |
| 2009/0240377 A1 | 9/2009 | Batzler et al. |
| 2011/0084844 A1 * | 4/2011 | Carnation .............. G08B 21/14 |
| | | 340/628 |
| 2012/0122040 A1 | 5/2012 | Xu et al. |
| 2012/0277972 A1 * | 11/2012 | Rayl ........................ F02D 37/00 |
| | | 701/102 |
| 2013/0110376 A1 | 5/2013 | Surnilla et al. |
| 2013/0168969 A1 | 7/2013 | Markoski |
| 2015/0036138 A1 * | 2/2015 | Watson .................. G01N 21/31 |
| | | 356/402 |
| 2015/0096352 A1 | 4/2015 | Peterson et al. |
| 2016/0258387 A1 | 9/2016 | Markoski |
| 2017/0110003 A1 | 4/2017 | Barson |
| 2017/0363022 A1 | 12/2017 | Tedder et al. |
| 2018/0208074 A1 * | 7/2018 | Lee ..................... B60L 11/1864 |
| 2018/0232860 A1 * | 8/2018 | Kozub .................... G06T 5/002 |
| 2018/0291822 A1 | 10/2018 | Wischstadt et al. |

OTHER PUBLICATIONS

International Search Report and Written Opinion, PCT/US2018/024855, Briggs & Stratton Corporation (Jul. 23, 2018).

* cited by examiner

CARBON MONOXIDE SENSOR FOR PORTABLE GENERATOR

CROSS-REFERENCE TO RELATED PATENT APPLICATIONS

This application claims the benefit of U.S. Provisional Application No. 62/512,623, filed May 30, 2017, which is incorporated herein by reference in its entirety.

BACKGROUND

The present invention generally relates to internal combustion engines. More specifically, the present invention relates to a carbon monoxide (CO) detection system for a portable generator powered by an internal combustion engine.

SUMMARY

One embodiment of the invention relates to a generator. The generator includes an internal combustion engine and a carbon monoxide (CO) sensor unit. The CO sensor unit includes a CO sensor controller including a CO sensing circuit configured to detect a level of CO and a shutdown circuit. The shutdown circuit is configured to receive a detected level of CO and calculate a trailing window average of the detected level of CO. The trailing window average includes an average of the detected level of CO over a predetermined sampling window. The shutdown circuit is further configured to determine whether to initiate a shutdown of the generator based on at least the calculated trailing window average and a predetermined trailing window average threshold and initiate the shutdown of the generator based on determining that the trailing window average exceeds the predetermined trailing window average threshold.

Another embodiment of the invention relates to a CO sensor system. The CO sensor system includes a CO sensor and a CO sensor controller. The CO sensor controller includes a CO sensing circuit configured to detect a level of CO and a shutdown circuit. The shutdown circuit is configured to receive a detected level of CO and calculate a trailing window average of the detected level of CO. The trailing window average includes an average of the detected level of CO over a predetermined sampling window. The shutdown circuit is further configured to determine whether to initiate a shutdown of an engine based on at least the calculated trailing window average and a predetermined trailing window average threshold and initiate the shutdown based on determining that the trailing window average exceeds the predetermined trailing window average threshold.

Alternative exemplary embodiments relate to other features and combinations of features as may be generally recited in the claims.

BRIEF DESCRIPTION OF THE DRAWINGS

The disclosure will become more fully understood from the following detailed description, taken in conjunction with the accompanying figures, in which.

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Figure 1:
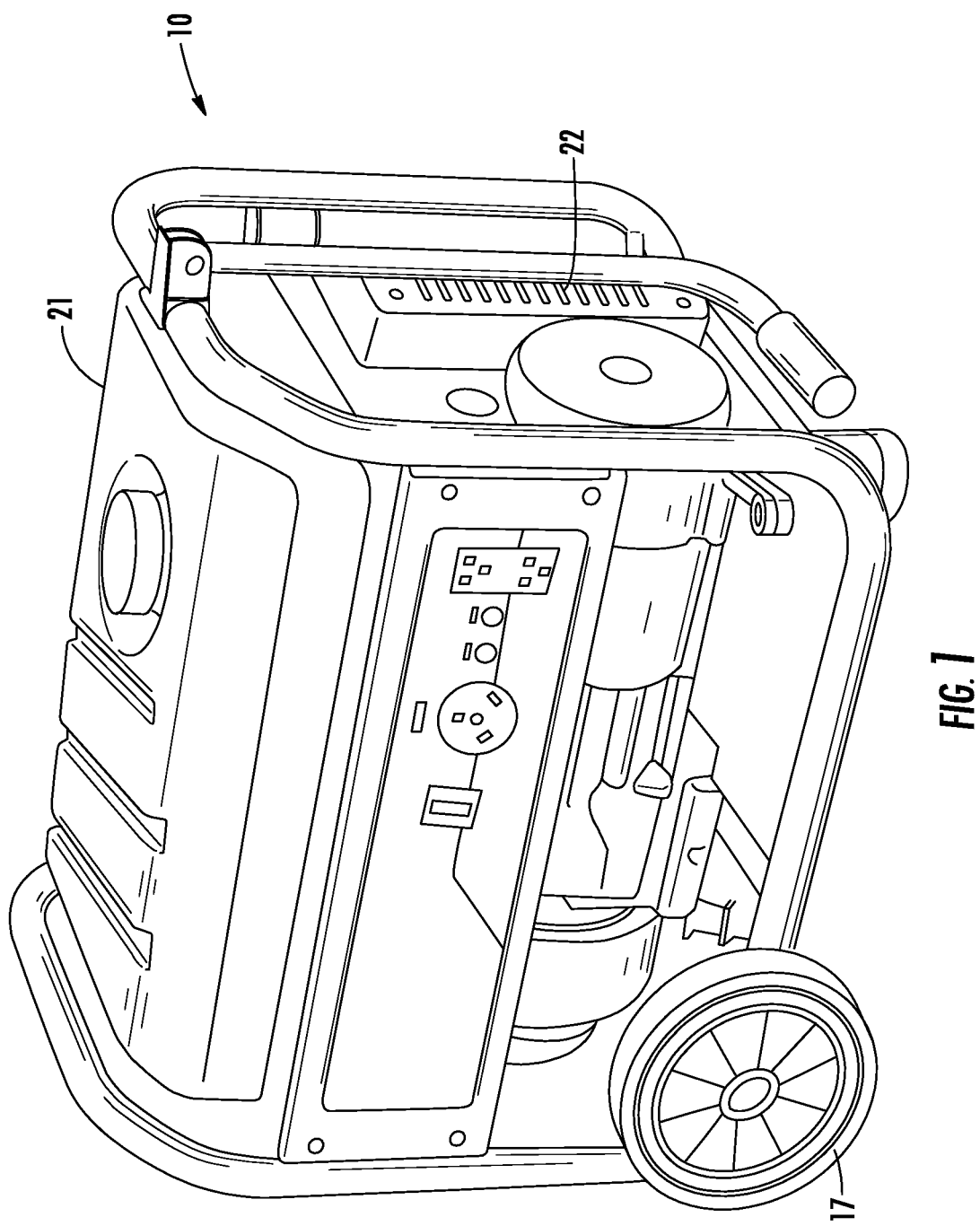
FIG. 1 is a perspective view of a generator according to an exemplary embodiment.
Figure 2:
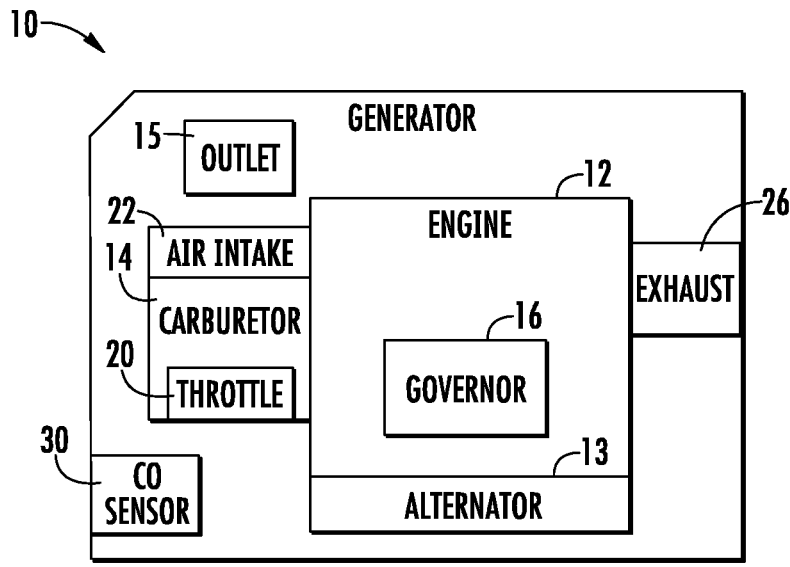
FIG. 2 is a schematic diagram of the generator of FIG. 1.

Referring to FIGS. 1-2, a generator is shown according to an exemplary embodiment. The generator 10 includes an engine 12, including a carburetor 14 or other air-fuel mixing device (e.g., electronic fuel injection, direct fuel injection, etc.), governor 16, throttle 20, air intake 22, exhaust outlet 26, and an alternator 13 driven by the engine 12. The alternator 13 produces electrical power from input mechanical power from the engine 12. The generator 10 additionally includes one or more outlets 15 for supply of the generated electrical power to an electrical device of a user's choosing. The generator 10 can also include one or more wheels 17 for portability. In some embodiments, a fuel tank 21 is positioned at the top of the generator 10 with the exhaust outlet 26 positioned below the fuel tank 21.

Air flows into the engine 12 from the air intake 22 and through the carburetor 14. As air passes through the carburetor 14, the air mixes with fuel entering the carburetor 14 from the fuel tank 21 and creates an air/fuel mixture that then enters the engine 12. The throttle 20 controls the flow of the air/fuel mixture that exits the carburetor 14. The governor 16 controls the position of the throttle 20 based on a detected load on the engine 12. The air/fuel mixture leaving the carburetor 14 is combusted in one or more cylinders of the engine 12 and exhaust gas from combustion leaves the engine 12 through the exhaust outlet 26. The exhaust gas is primarily made up of nitrogen, water vapor, and carbon dioxide, but a portion of the exhaust gas may be carbon monoxide (CO) from incomplete combustion. Operation of a generator (or any other equipment powered by an engine) in a non-ventilated or insufficiently ventilated enclosed or partially enclosed space (e.g., volume), such as a garage, home, storage unit, pop-up tent, etc., can result in accumulation of CO within the space over time.

As shown in FIG. 2, the generator 10 includes a CO sensor 30 configured to detect the level or concentration of CO (e.g., parts per million (ppm)). Additionally, the CO sensor 30 may be used with other types of outdoor power equipment. Outdoor power equipment includes lawn mowers, riding tractors, snow throwers, pressure washers, portable generators, tillers, log splitters, zero-turn radius mowers, walk-behind mowers, riding mowers, industrial vehicles such as forklifts, utility vehicles, etc. Outdoor power equipment may, for example, use an internal combustion engine to drive an implement, such as a rotary blade of a lawn mower, a pump of a pressure washer, the auger a snow thrower, the alternator of a generator, and/or a drivetrain of the outdoor power equipment. Portable jobsite equipment includes portable light towers, mobile industrial heaters, and portable light stands.

Figure 3:
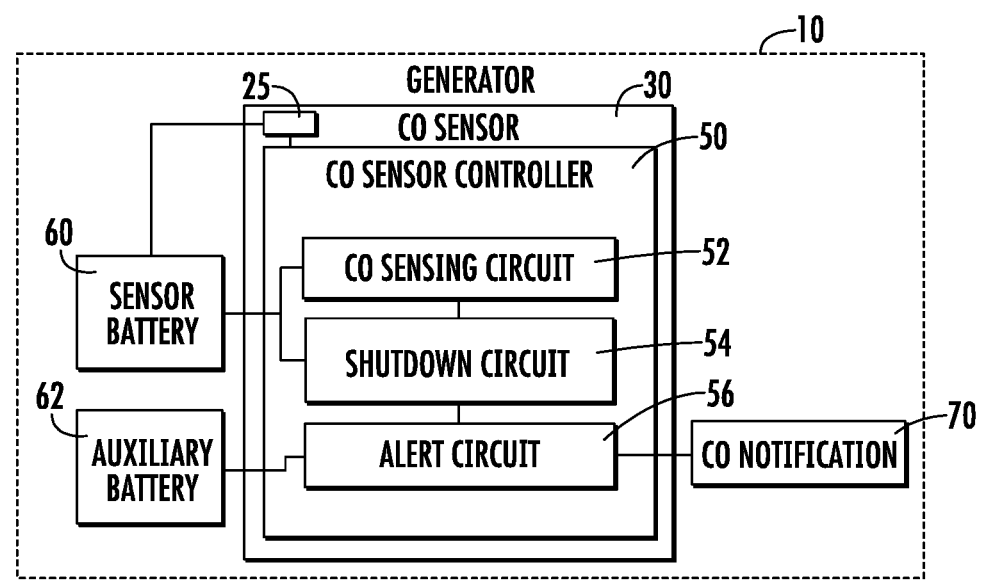
FIG. 3 is a schematic diagram of a carbon monoxide detection sensor of the generator of FIG. 1.

Referring now to FIG. 3, a schematic diagram of the CO sensor 30 is illustrated, according to an exemplary embodiment. In some embodiments, the CO sensor 30 includes a metal oxide gas sensor unit 25. The metal oxide gas sensor unit 25 detects CO concentration via a gas sensitive film that is composed of tin or tungsten oxides. The sensitive film reacts with CO to determine CO concentration at the sensor unit 25. In other embodiments, the CO sensor 30 can include an electrochemical sensor. The electrochemical sensor measures the concentration of CO at the sensor by oxidizing or reducing the gases at an electrode and measuring the resulting current.

Figure 7:
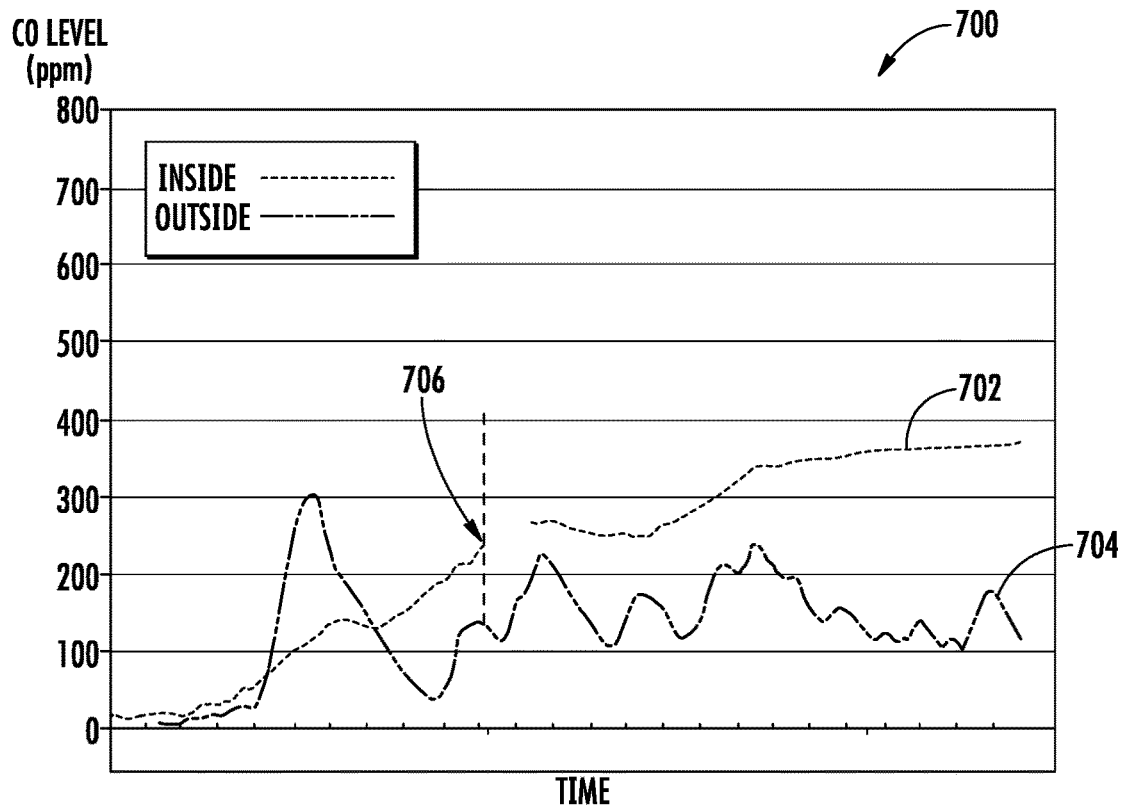
FIG. 7 is a graph of generator operating time versus carbon monoxide detection levels for an outside condition and an inside condition.

The CO sensor 30 alerts a user to an elevated concentration of CO exceeding the predetermined threshold and controls the shutdown of the generator 10 in these instances. Additionally, as discussed further herein, the CO sensor 30 includes control circuitry to determine when detections of an elevated CO concentration may be fleeting (e.g., short spikes in signal readings). Fleeting elevated CO concentration detections may be due to movement of the surrounding air rather than unwanted accumulation of CO over a period of time. Movement of the surrounding air can, under certain conditions, introduce the CO sensor 30 to CO laden exhaust from the generator 10. This can cause transient spikes in the CO level as read by the sensor 30. For example, referring to the graph in FIG. 7, an example comparison between sensed CO levels in an inside (e.g., enclosed) area (shown by inside generator curve 702) and in an outside (e.g., open-air) area (shown by outside generator curve 704) are shown. As shown, the CO levels for the inside generator rise steadily over time and the CO levels for the outside generator fluctuate between high and low sensed CO levels. Further, the inside generator curve 702 indicates a shutdown at point 706. For example, as described further herein, the generator 10 may have shut down at point 706 due to the transient summed array reaching the value of 40 and the TWA value exceeding 200 ppm of CO.

The CO sensor 30 includes or is coupled to a CO sensor controller 50 configured to control the operations of the CO sensor 30, including but not limited to, timing of generator shutdown and alerts, transmitting an alert to a user, triggering a visual alarm (e.g., indicator light), triggering an audible alarm (e.g., alarm bell), shutting down the generator, etc. To perform the functions described herein, the CO sensor controller 50 includes a processing circuit, which includes a processor and a memory. The processor may be implemented as a general-purpose processor, an application specific integrated circuit (ASIC), one or more field programmable gate arrays (FPGAs), a digital signal processor (DSP), a group of processing components that may be distributed over various geographic locations or housed in a single location, or other suitable electronic processing components. The one or more memory devices (e.g., RAM, NVRAM, ROM, Flash Memory, hard disk storage) may store data and/or computer code for facilitating the various processes described herein. Moreover, the one or more memory devices may be or include tangible, non-transient volatile memory or non-volatile memory. Accordingly, the one or more memory devices may include database components, object code components, script components, or any other type of information structure for supporting the various activities and information structures described herein.

In some embodiments, the CO sensor 30 and CO sensor controller 50 form a CO sensing system. The CO sensor 30 and CO sensor controller 50 can be packaged as a unit within a shared housing or packaged separately for detection of CO. In some embodiments, the CO sensor controller 50 is incorporated into a controller tasked with other control responsibilities in an end product (e.g. incorporated into the engine controller or other controller of an automobile). In this way, the CO sensor 30 and/or CO sensor controller 50 can be used to detect CO and shut down an engine used with any type of equipment. For example, the CO sensor 30 and/or CO sensor controller 50 can be used on a vehicle to detect CO levels and/or accumulation resulting from vehicle exhaust and shut down an engine on the vehicle in response to a determination of accumulation or high levels of CO.

The CO sensor controller 50 includes a CO sensing circuit 52, a shutdown circuit 54, and an alert circuit 56, with all such circuits communicably coupled to each other. The CO sensing circuit 52 is configured to receive sensor output values from the CO sensor 30 relating to the detected CO concentration and communicate the CO concentration to the shutdown circuit 54 and alert circuit 56. Accordingly, the CO sensing circuit 52 is communicably and operatively coupled to the shutdown circuit 54 and alert circuit 56 to provide the CO concentration values. In some embodiments, the CO concentration values may be provided in terms of output voltage values which are proportional to the CO ppm values. The CO sensor controller 50 may additionally include a database configured to store sensed CO values over time and corresponding response actions (e.g., generator shutdown, alert transmission, alert signal, self-diagnostics, etc.). The CO sensor controller 50 may also include a temperature sensor configured to sense the ambient temperature surrounding the generator 10. The sensed temperature values can be used to adjust the CO sensed values to accommodate for sensed temperature. The sensed temperature may be an indication of a generator running environment as the sensed temperature surrounding a generator inside may be higher than that of a generator running outside.

The shutdown circuit 54 is configured to receive the detected CO values from the CO sensing circuit 52, determine whether the generator 10 is likely in an enclosed space, an open space, a small enclosed space, a large enclosed space, a semi-enclosed space, or outdoor space and determine whether to shut down the generator 10 and/or provide a triggered alarm response to the detection. Upon receiving the detected CO concentration values (e.g., correlating output voltage values) from the CO sensor 30, the shutdown circuit 54 first determines if the generator 10 is likely in an enclosed space or an open space. Depending on indications of whether the generator 10 is in an open or enclosed space, the shutdown circuit 54 will treat sensed CO concentration data differently. To determine the environment of the generator 10, the shutdown circuit 54 may use a variety of methods. In many of the methods, the shutdown circuit 54 uses time lapse information to perform calculations. Accordingly, a timing circuit may be included with the generator 10 to determine the amount of time the generator 10 has been running. To determine run time, electrical output from the generator, spark plug data, and/or electric starter data may be used to determine the start of the generator operation, the duration of generator operation, the number of engine starting or stopping events within a certain period of time, etc. Additionally, calculations may be reset due to a sensed movement of the generator 10. Movement of the generator 10 can be sensed via a piezoelectric sensor positioned on the generator 10 configured to measure acceleration data.

The shutdown circuit 54 may additionally set an absolute maximum CO concentration threshold such that upon reaching the threshold, the generator 10 is shut down. Accordingly, at any point in time regardless of the environment in which the generator 10 is positioned, when an absolute CO threshold concentration (e.g., >300 ppm of CO) is detected, the generator 10 is shut down.

In some embodiments, the shutdown circuit 54 also uses the overall lapsed time since the generator 10 was started to determine a sensed value threshold for shut down. For example, for a time period of less than twelve minutes, the shutdown circuit 54 uses one set of threshold values to determine when to shut down the generator 10 and for one or more subsequent operating periods (e.g., greater than twelve minutes, etc.), the shutdown circuit 54 uses a different set of threshold values. For the initial operating period, the shutdown circuit 54 has lower threshold values for triggering a shutdown or alarm than the subsequent operating periods. Any false alarm or shutdown triggers may be less inconvenient to a user while the user is still near the generator 10 (e.g., less time has passed), than if the user has already left the area. In other embodiments, other time periods can be used. Once the generator 10 moves into subsequent operating periods, the controller can be more confident that the generator is not operating in an enclosed space and can reduce the sensitivity and reduce the occurrence of unwanted shutdowns. Because CO typically accumulates quickly in an enclosed space, it is beneficial to be relatively sensitive to elevated CO concentrations in that environment to shut down the generator.

In addition to monitoring the current CO concentration value, the shutdown circuit 54 calculates and monitors a trailing window average (TWA) of the sensed CO concentration values. To continually monitor the TWA, the shutdown circuit 54 uses current and past sensed CO concentration values for a single generator run. In this regard, the shutdown circuit 54 may temporarily store the readings relating to one or more data samples in a database incorporated with the CO sensor controller 50. To calculate the TWA, the shutdown circuit 54 uses the equation below for each sample reading time frame.

$$TWA = TWA_{old}\left(\frac{n_{TWA} - 1}{n_{TWA}}\right) + ppm_{current\ reading}\left(\frac{1}{n_{TWA}}\right)$$

In the above equation, "$TWA_{old}$" is the prior loop value of the TWA, "$n_{TWA}$" is the number of loops over which the value is averaged, and "$ppm_{current\_reading}$" is the sensed CO concentration value.

By determining the TWA of the sensed CO concentration values using an equation such as the one above, as well as other factors described herein, the shutdown circuit 54 determines whether the generator 10 is in an enclosed space (e.g., garage) and potentially experiencing settled accumulations of CO or in an open space (e.g., outside) and experiencing brief spikes in readings of the CO concentrations (e.g., due to air movement surrounding the generator 10). The TWA of the sensed values indicates the amount of data points that are either rising or falling with respect to past sensed values, and thus, can be used as a factor in determining if accumulation is occurring over time.

The current loop calculated TWA value is compared against the prior loop TWA value to set a binary transient value. A binary transient value is set to either a value of one or a value of zero based on the relationship between the prior loop TWA values and the current loop calculated TWA values. If the current TWA loop value is greater than the TWA value by at least a threshold value (e.g., 1 ppm), the binary transient value is set to one. If the current TWA loop value is less than a threshold value above the prior loop TWA value, the binary transient value is set to zero (see FIG. 9). As an example, the threshold value can include 1 ppm of CO. In another example, the threshold value is more or less than 1 ppm of CO. In other examples, the threshold value may be expressed as a percentage (e.g., +/−5% of the TWA value). The binary transient values are stored in a pre-sized array and all stored binary transient values in the array are summed to calculate a summed array value. The summed array value is used in connection with other factors to determine whether to shut down the generator 10, as described further herein. The members of the array and therefore the sum of the array are reset to zero upon detection of a current TWA value less than the threshold above the prior TWA. The size of the array corresponds to the number of data points desired to be summed to calculate a summed array value. For example, the pre-sized array may include 40 data points, such that the summed array value includes the sum of all 40 data points.

As described further herein, various conditions may trigger a generator shutdown and/or alert. In one condition representing a small or mid-size enclosure with rapid CO level rise, if the generator is still in an initial operating mode (e.g., start-up mode, less than a predetermined time period), the TWA equals or exceeds a first TWA threshold, and the summed array value equals a predetermined sum threshold, a generator shutdown and/or alert is triggered. As an example, in this condition, the initial operation may last for approximately twelve minutes, the first TWA threshold may be 200 ppm of CO, and the predetermined sum threshold equals 40 (equaling the number of data points in the binary transient array). Accordingly, in this example, if the generator has been running for less than twelve minutes, the TWA value equals or exceeds 200 ppm of CO, and the summed value equals 40, a shutdown and/or alert is triggered. If one or more of these conditions is not met, the shutdown and/or alert is not triggered.

In a second condition, if the generator is past an initial operating condition (e.g., more than a predetermined time period of twelve minutes) and the TWA equals or exceeds a second TWA threshold (e.g., equal to or exceeding 300 ppm), a shutdown and/or alert is triggered. As an example, for a shutdown and/or alert to be triggered in this condition, the generator has been running for more than twelve minutes and the TWA exceeds a 300 ppm of CO threshold. Regardless of whether in a start-up mode (e.g., less than twelve minutes) or in a continuous mode (e.g., more than twelve minutes), a TWA value exceeding 300 ppm invokes a shutdown. In some embodiments, the number of loops used to calculate the TWA value in a start-up mode is 5 loops and the number of loops used to calculate the TWA value in a continuous mode is 70 loops.

Another condition of shutdown, which is configured to protect against semi-enclosed generator running (e.g., under a pop-up canopy or in a garage with an open garage door), includes monitoring the TWA in longer windows of time and if during the monitoring window the TWA remains above a certain threshold of CO, a shutdown procedure will be triggered. For example, if the TWA exceeds a limit of 200 ppm for more than 120 loops (not necessarily contiguous), a shutdown is invoked. The count of the loops with a TWA value of greater than 200 ppm may be referred to as the "alcove count." The alcove count is reset to zero if the current TWA value is more than 75 ppm below the maximum TWA value recorded since the start of the generator 10. The alcove count protection runs in both a start-up mode and a continuous mode.

The combination of parameters including generator runtime, TWA, summed array value, and currently sensed CO level (ppm) can be combined to best guard against CO accumulations during enclosed space running, while minimizing nuisance shutdowns. During initial operation (e.g., less than twelve minutes), the TWA of sensed CO levels is monitored to a higher threshold. As an example, a generator shutdown is triggered if a TWA of CO concentrations is greater than or equal to a threshold of 200 ppm of CO and the summed array value is equal to the array size (e.g., summed array value equals 40) or if the TWA is greater than or equal to a threshold of 300 ppm of CO. Conversely, if run-time is greater than twelve minutes, a generator shutdown is not triggered for detected CO concentrations until a TWA of sensed CO levels is higher than 300 ppm.

To provide further protection against nuisance shutdowns during the initial operation of the generator (e.g., during a start-up mode, less than twelve minutes), if the TWA of the sensed CO levels is monitored to drop by more than a predetermined threshold (e.g., 75 ppm) below the maximum TWA value since the startup of the generator 10, the monitoring mode of the generator is changed from a start-up mode to a continuous mode, as described further herein with regard to FIG. 6. The start-up mode is the monitoring mode during the initial operation of the generator 10 and the continuous monitoring mode is the monitoring mode after the initial operation of the generator 10. If the TWA of the sensed CO levels drops by more than the threshold, this is an indication of the generator 10 being located in an open-air area, where air movement may cause great fluctuations in the sensed CO levels. By changing the monitoring mode from a start-up mode to a continuous mode (e.g., from a more stringent to a less stringent monitoring mode), less nuisance shutdowns may occur.

In some embodiments, the shutdown circuit 54 may additionally or alternatively use other calculation methods to determine whether the generator 10 is in an enclosed or an open space. The shutdown circuit 54 may use any method to detect and amplify the characteristics (e.g., choppy versus smooth) of the detected CO concentration versus time curve. For example, variance, standard deviation, variance of the first derivative, peak-to-peak range, curve kurtosis, or other custom functions may be used to determine the environment of the generator 10.

The shutdown circuit 54 can use various other sensors to determine whether the generator 10 is in an enclosed or an open space. The sensors can include, but are not limited to, an ambient lighting sensor, an acoustic sensor, radar sensor, wind speed sensor, Global Positioning System (GPS) mapping, and so on.

Once the shutdown circuit 54 has determined whether the generator 10 is in an enclosed or open space, the shutdown circuit 54 triggers shutdown and/or alerts upon detection of a predetermined threshold for that environment. In this regard, the shutdown circuit 54 is coupled to an engine shutdown circuit of the engine 12 to complete a shutdown procedure. The shutdown procedure may include grounding the generator ignition for a period of time (e.g., 10 seconds) until the engine 12 is turned off. The shutdown circuit 54 is also communicably and operatively coupled to the alert circuit 56 to communicate an indication that a threshold level has been reached for an alert to be triggered. The alert may be paired with a shutdown of the generator 10 and/or a warning of potentially elevated CO concentration without shutting down the generator 10. Accordingly, the alert may include illuminating light-emitting diodes (LEDs) on the user interface of the generator 10 to indicate that the generator is being or has been shut down.

After the generator has been shut down, the shutdown circuit 54 is further configured to remain in an active mode, where the shutdown circuit 54 is actively monitoring and preventing restart of the generator 10, for a period of time (e.g., 15 minutes). Accordingly, if a user tries to restart the generator 10 during this time, the shutdown circuit 54 will prevent the starting of the generator 10 and effectively "lock-out" the user from using the generator 10 during that time. As such, a user is prevented from restarting the generator 10 and further accumulating CO during times when the generator has been shut down based on high sensed CO concentrations. In some embodiments, instead of locking out the user, the generator 10 may be allowed to restart briefly, but immediately shutdown if a CO level threshold trigger is detected again. This may be advantageous to power management (e.g., battery life) of the system.

The alert circuit 56 is configured to communicate with the shutdown circuit 154 to receive an indication that the generator 10 has been shut down due to sensed CO accumulation or an indication of an elevated CO concentration. The alert circuit 56 is additionally configured to trigger a CO notification 70 (e.g., alarm system) on the generator including, but not limited to, an indicator light and an audible alarm. In this configuration, if the user is signaled that the shutdown is due to CO emissions build-up in a non-ventilated space, the user is less likely to try to start the generator back up. The alert circuit 56 may trigger varying levels of alarms corresponding to the sensed concentration of CO, with alarm severity increasing with the increasing CO concentration (e.g., warning light, warning audible alarm and then shut down, etc.). In some embodiments, the alert system is powered by a separate power supply than the sensing element (e.g., sensor unit 25) to prolong the shutdown capability of the system, described further herein.

In some embodiments, the alert circuit 56 is configured to switch over a mechanical switch to an elevated CO concentration indication position when a shutdown of the generator 10 occurs due to the detection of accumulated CO. Accordingly, the user will be notified of the CO detection by the physical location of the switch even though the generator 10 has been shut down and no electrical (e.g., sound or light) indication may be present. In the case of a shutdown switch, before starting the generator 10 back up after a shutdown, the user must first physically move the switch from the elevated CO concentration indication position back to an operating position. In some embodiments, the generator 10 may additionally include tamper resistant sensors. Accordingly, a user cannot easily disconnect or circumvent the sensors described herein. For example, power and communication wires to and from the CO sensor 30 may be combined in a single wire harness.

In some embodiments, the alert circuit 56 is additionally configured to communicate with a mobile device to alert a user that the generator 10 has been shut down due to sensed CO accumulation. Accordingly, the user may be alerted on the mobile device while the user is away from the generator 10 and can proceed with caution if re-entering the enclosed space.

One or more batteries are included to power the components of the CO sensor 30 and CO sensor controller 50. In some embodiments, the batteries are lithium-ion coin cell batteries. In other embodiments, the batteries may use different battery chemistries and/or structural configurations. A sensor battery 60 is coupled to the CO sensor unit 25, the CO sensing circuit 52, and the shutdown circuit 54 to provide power to the sensing, detection, and shutdown operations of the generator 10. The sensor battery 60 continues to provide power to the CO sensor unit 25 even when the generator 10 is shut down. This way, the CO sensor unit 25 is still actively monitoring CO concentration (e.g., via pulse detection) when the generator 10 is not running. The continuous operation of the CO sensor unit 25 allows the unit 25 to continue to monitor the CO concentration in the vicinity of the generator 10 (e.g., every three minutes) and prevents the unit 25 from resetting the baseline CO reading to zero ppm upon turning off power from the generator to the sensor unit 25. Without continuous supply of power to the sensor unit 25 from the sensor battery 60, the sensor unit 25 may normalize the CO reading to zero ppm upon receiving power (even in areas with CO present), and accordingly, the CO reading may be skewed if power is not continuously supplied to the CO sensor unit 25.

An auxiliary battery 62 can also be coupled to the CO sensor 30 to provide power to the auxiliary systems included with the CO sensor 30, such as the alert circuit 56 and the CO notification 70 (e.g., alert light, audible alarm, sensor self-diagnostics, etc.). Like the sensor battery 60, the auxiliary battery 62 may also provide continuous power to the auxiliary systems of the sensor 30. Accordingly, an alert may still be transmitted, sounded, lit, etc. and self-diagnostics are still performed when the generator 10 is off.

The CO sensor 30 is continuously running self-diagnostics. If a problem is detected, such as low sensor battery, low alert battery, missing sensor module, the sensor is shorted, the sensor electrolyte is dried out, the sensor has reached the end of its sensor life, etc., an alert notification is triggered (e.g., red LED is illuminated once every 10 seconds) and the ignition is grounded to shut down the generator 10. The sensor failure mode triggers a lock-out condition such that a user cannot restart the engine 12 until the CO sensor 30 (e.g., sensor unit) is replaced. In some embodiments, instead of locking out the user, the generator 10 may be allowed to restart briefly, but immediately shutdown if a CO level threshold trigger is detected again.

Figure 4:
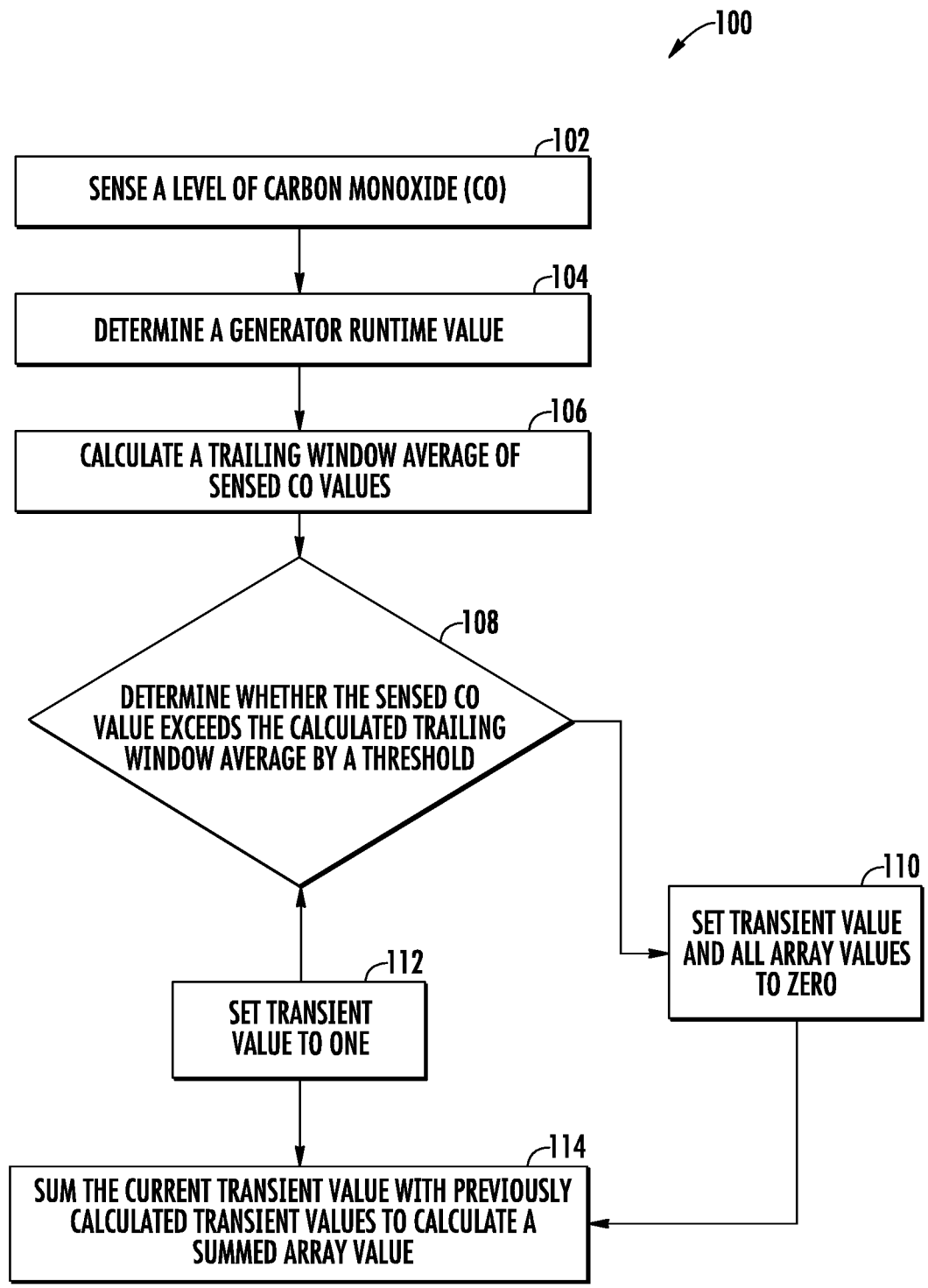
FIG. 4 is a flow chart of a method of determining a transient value and calculating a sum of transient values, according to an exemplary embodiment.

Referring to FIG. 4, a method for setting and summing binary transient values is shown, according to an exemplary embodiment. The method 100 includes sensing a CO concentration level at 102. The CO concentration level is sensed by the CO sensor 30. The CO concentration level is received by the shutdown circuit 54 for monitoring, as described further herein.

A generator runtime value is determined at 104. The generator runtime value may be tracked by a timing circuit incorporated with the CO sensor controller 50. Accordingly, a timing circuit may be included with the generator 10 to determine the amount of time the generator 10 has been running. As noted above, to determine run time, electrical output from the generator, spark plug data, and/or electric starter data may be used to determine the start of the generator operation, the duration of generator operation, the number of engine starting or stopping events within a certain period of time, etc.

A TWA of sensed CO concentration values is calculated at 106. As shown above in the equation for calculating TWA, the TWA is determined using the current CO concentration level, a prior loop value of TWA, and the number of loops over which the value is averaged. Next, it is determined whether the sensed CO concentration value is greater than a threshold above the calculated TWA at 108. If the sensed CO concentration value is less than the threshold above the TWA, the transient value is set to zero and all array values are set to zero (e.g., effectively resetting the summed array value to zero) at 110. If the sensed CO concentration value is greater than a threshold above the TWA, the transient value is set to one at 112. The current transient value is then summed with the previously calculated transient values to determine a summed array value at 114.

Figure 5:
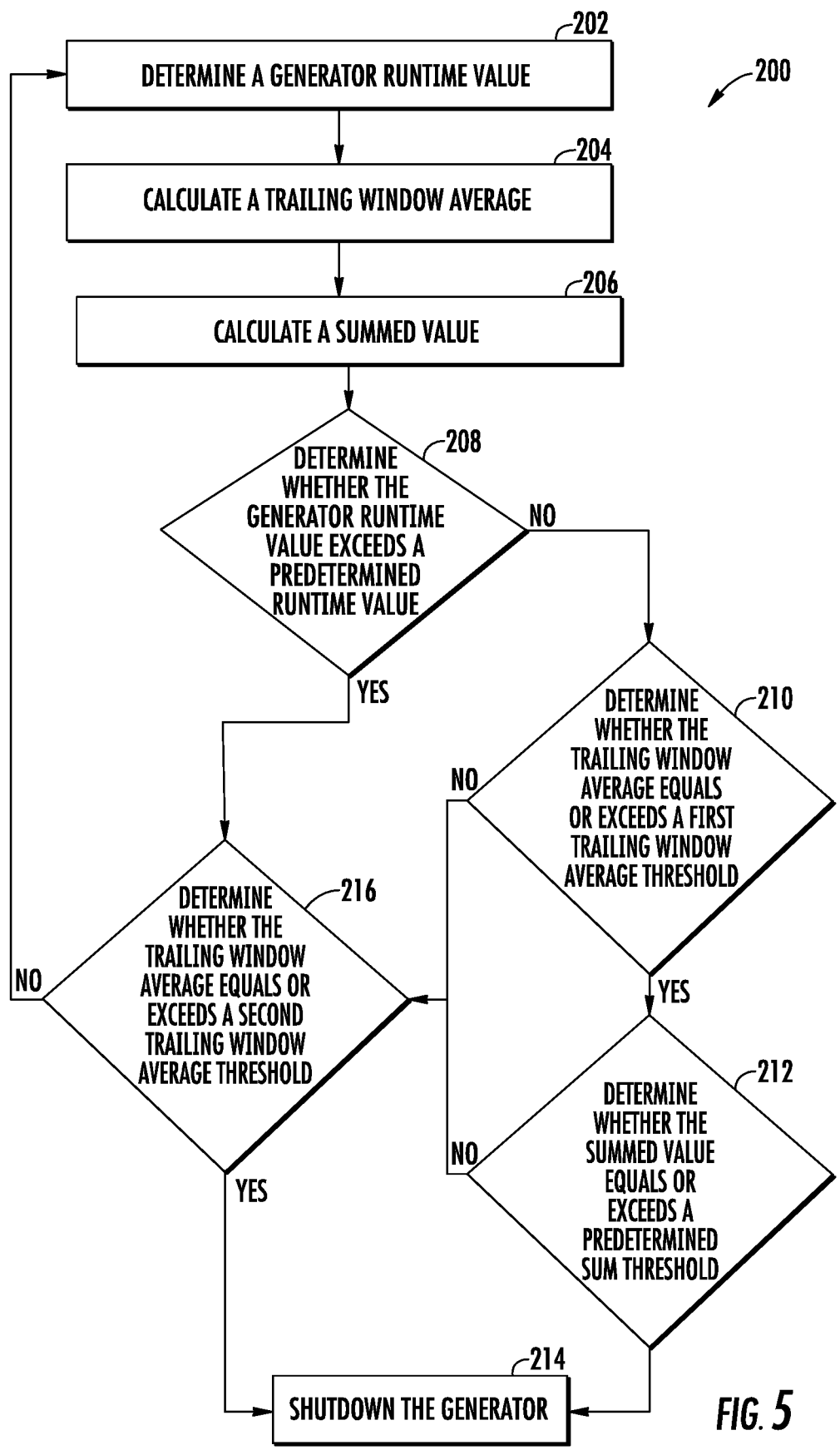
FIG. 5 is a flow chart of a method of monitoring CO levels and shutting down the generator, according to an exemplary embodiment.

Referring to FIG. 5, a method for determining whether to shut down the generator is shown, according to an exemplary embodiment. The method 100 includes determining a generator runtime value at 202. The generator runtime value may be determined similarly to step 104 in method 100 (FIG. 4). The TWA is calculated at 204. The TWA may be calculated in accordance with the equation above and step 106 of method 100 (FIG. 4). The summed array value is calculated at 206. The summed array value may be calculated similarly to steps 108-114 in method 100 (FIG. 4).

Next, it is determined whether the generator runtime value exceeds a predetermined runtime value at 208. In one embodiment, the predetermined runtime value is twelve minutes. In other embodiments, the predetermined runtime value can be more or less than twelve minutes (e.g., between 10 and 20 minutes).

If the generator runtime value does not exceed the predetermined runtime value at 208, it is determined whether the TWA equals or exceeds a first TWA threshold at 210. As an example, the first TWA threshold may be set to 200 ppm of CO. The first TWA threshold may correlate to a lower TWA CO concentration limit. This lower limit of CO concentration may be used during a start-up monitoring mode. The start-up monitoring mode is used during runtime of the generator under the predetermined runtime value (e.g., less than six minutes) and in combination with the summed array value described below to determine whether to shut down the generator or provide a notification of high levels of CO concentration.

If the TWA equals or exceeds a first TWA threshold at 210, it is determined whether the summed value is equal to a predetermined sum threshold at 212. In an exemplary embodiment, the summed value being equal to the sum threshold indicates that all numbers in the transient array are equal to one. As an example, with the 48 data point array described above, the sum threshold would equal 40 such that if all data points in the array are equal to one, the sum array is equal to 40 and thus, equal to the sum threshold. In other embodiments, the determination may include whether the summed value is exceeds a predetermined sum threshold, where the sum threshold is less than the size of the array.

If the TWA equals or exceeds the first TWA threshold at 210 and the summed value is equal to the predetermined sum threshold at 212, a CO notification is triggered and/or the generator is shut down at 214. In some embodiments, step 214 includes communicating an indication of the presence of CO concentration to the alert circuit 56. The alert circuit 56 and various shutdown and notification arrangements are described further herein.

If the generator runtime value does not exceed the predetermined runtime value at 208, it is determined whether the TWA equals or exceeds a second TWA threshold at 216. The second TWA threshold may correlate to a higher TWA CO concentration limit. This higher limit of CO concentration may be used during a continuous monitoring mode. The continuous monitoring mode is used during runtime of the generator exceeding the predetermined runtime value (e.g., over six minutes). If the TWA equals or exceeds the second TWA threshold, a CO notification is triggered and/or the generator is shut down at 214.

If the variance is calculated to be relatively high, the shutdown circuit 54 determines that the generator 10 is positioned in an open environment and may use a different sensed CO threshold to shut down the generator 10 than if the variance is calculated to be relatively low. As an example, if the variance is calculated to be relatively low, the shutdown circuit 54 determines that the generator 10 is likely positioned in an enclosed space and shuts down the generator 10 at a lower CO ppm reading or within a smaller time frame than if determined to be in an open space.

Figure 6:
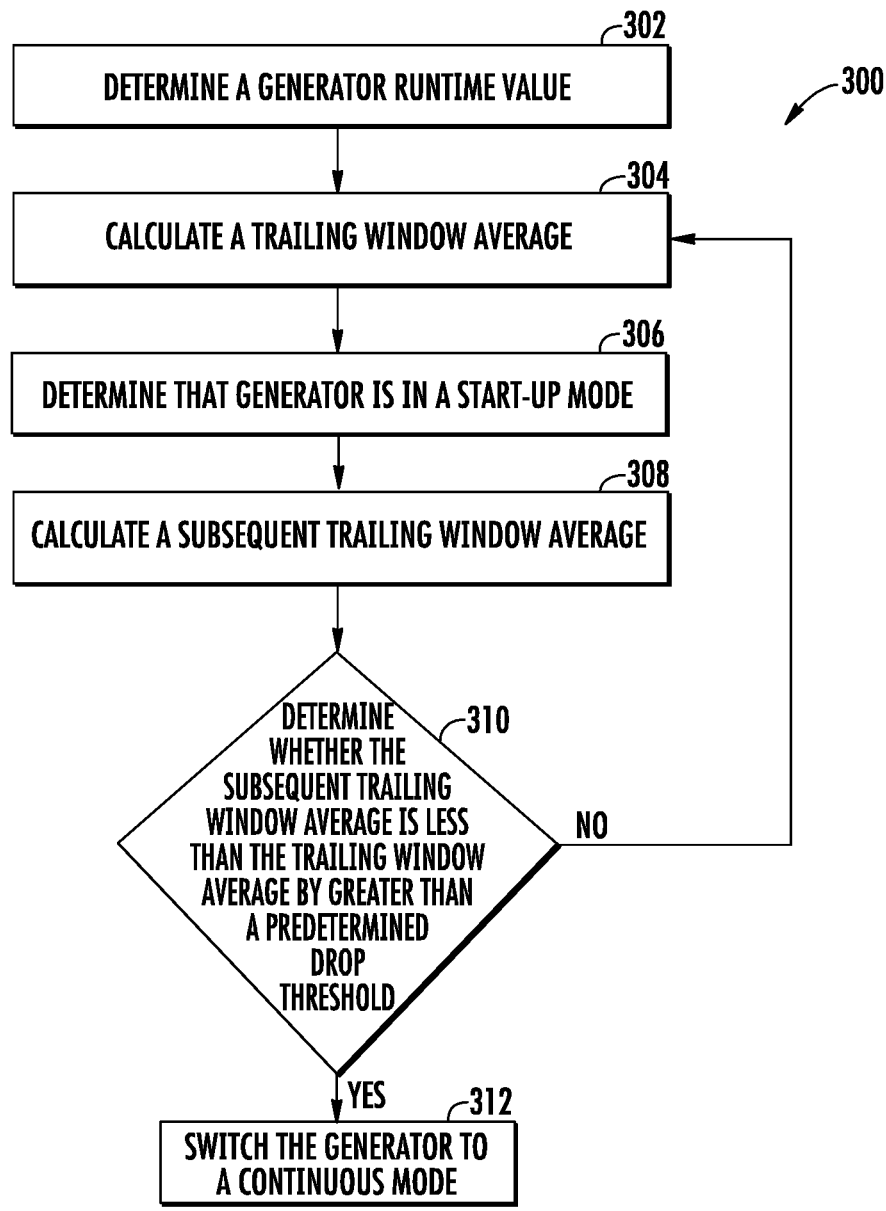
FIG. 6 is a flow chart of a method of transitioning the generator CO sensing mode from a start-up mode to a continuous mode, according to an exemplary embodiment.

Referring to FIG. 6, a method of switching from a start-up mode to a continuous mode for CO concentration level monitoring is illustrated, according to an exemplary embodiment. The method 300 includes determining a generator runtime value at 302 and calculating a TWA at 304, which may be completed in accordance with steps 104 and 106 of method 100, respectively.

Next, it is determined whether the generator is in a start-up mode at 306. The generator is in a start-up mode during the first predetermined time period of running (e.g., the predetermined generator runtime value in method 200). Accordingly, a start-up mode can be determined by comparing the first predetermined time period against the generator runtime value. If the generator runtime value is less than the first predetermined time period, the generator is in a start-up mode. If the generator runtime value is greater than the first predetermined time period, the generator is not in a start-up mode (e.g., is in a continuous monitoring mode).

A subsequent TWA is calculated at 308. The subsequent TWA is calculated in the same manner as the TWA value at step 304 and additionally includes the calculated TWA value of step 304 as the previous loop TWA value ($TWA_{old}$) in the TWA calculation above.

It is determined whether the subsequent TWA is less than the TWA by greater than a predetermined drop threshold at 310. As an example, the predetermined drop threshold may be 75 ppm. The predetermined drop threshold may be more or less than 75 ppm. If the subsequent TWA is less than the TWA by greater than the predetermined drop threshold, the generator is switched into a continuous monitoring mode. Accordingly, in the example, if the subsequent TWA value is less than the TWA by more than 75 ppm, the generator is switched into a continuous monitoring mode at 312.

The continuous monitoring mode is the CO level monitoring mode when the generator has been running for longer than the first predetermined time period (e.g., six minutes), as discussed above with regard to step 306. After the first predetermined time period, the monitoring mode for the generator switches from a start-up mode to a continuous mode. Using the method 300 described above, the time the generator is in the start-up mode may be shortened due to an indication of a sudden high drop-off in CO levels. A sudden high drop-off in CO levels may be an indication that the generator is positioned in an outside, non-enclosed area. The switchover from the start-up mode to a continuous mode due to a high drop-off in CO levels regardless of generator runtime may protect against nuisance shutdowns of the generator. Allowing for switchover from the start-up mode to a continuous mode due to high drop-offs in CO levels also allows for a longer start-up mode run time (e.g., six minutes) where a generator running in a particularly large space (e.g., parking garage, construction site) that may be slow to accumulate concentrations of CO can be monitored.

Figure 8:
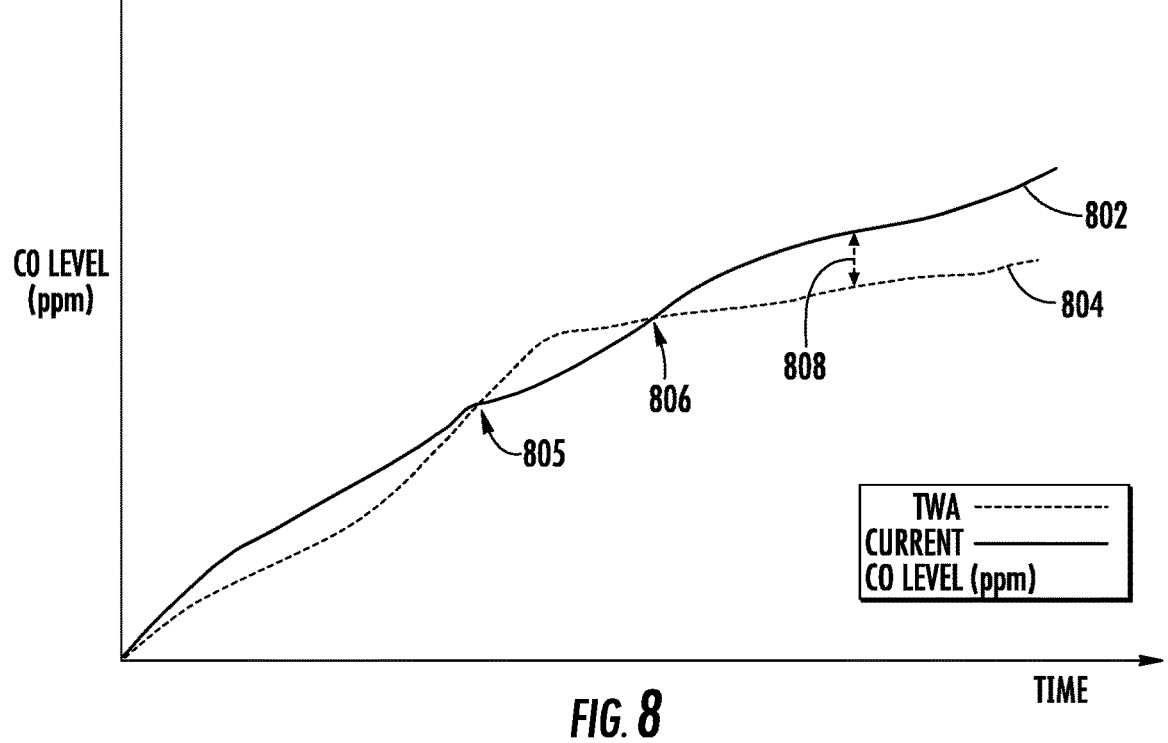
FIG. 8 is a graph of generator operating time versus carbon monoxide detection levels.

Referring to FIG. 8, a graph of generator run time versus sensed CO levels is illustrated. Graph 800 illustrates a current CO level curve 802 graphed against a calculated TWA curve 804. The CO level curve 802 increases more rapidly as the TWA curve 804 steadily increases. As shown, the CO level curve 802 starts above the TWA curve 804, dips below the curve 804 at point 805, surpasses the TWA curve 804 again at point 806, and remains above the TWA curve 804 for the remainder of the graph 800. This type of behavior may be indicative of an enclosed running generator due to the steady rise of CO levels. The CO level curve 802 reaches above a threshold above the TWA curve 804 shown as 808. At this point, as described above, the binary transient values are set to a value of one. Prior to this, the binary transient values were set to a value of zero. Accordingly, the steady rise of the CO level curve 802 will result in the summed array value increasing over time.

Figure 9:
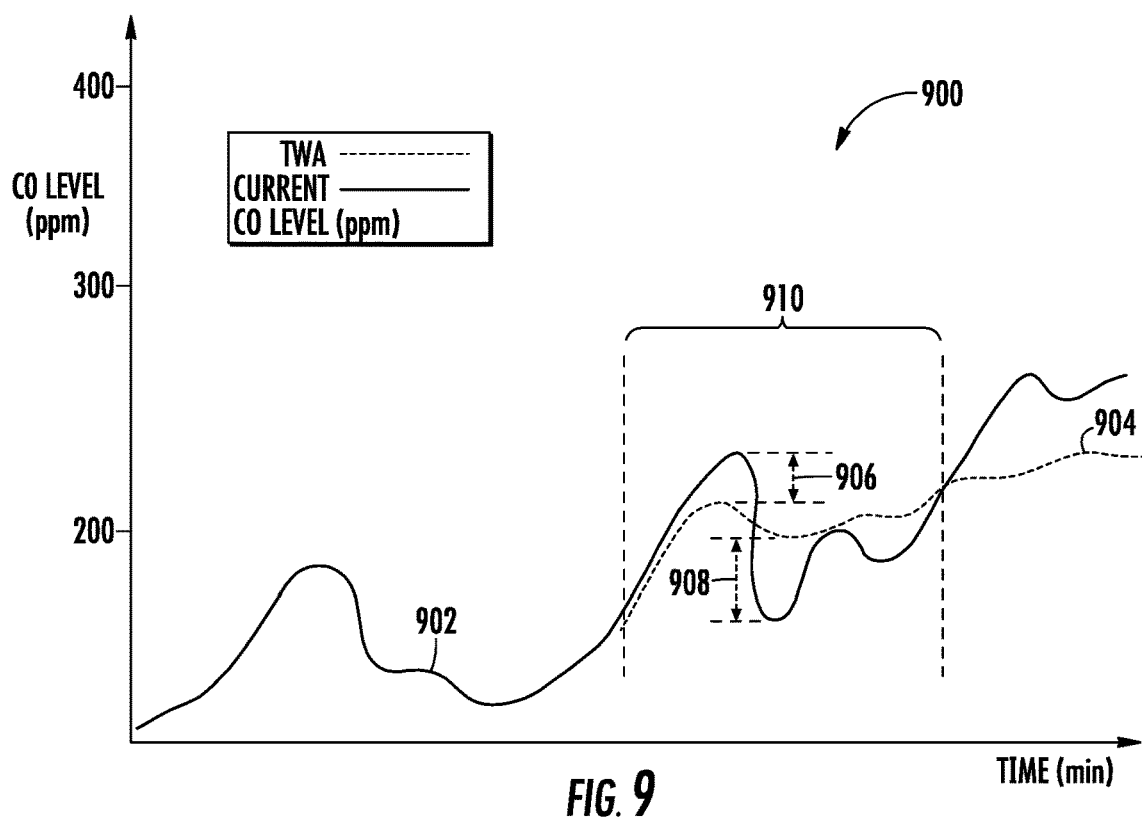
FIG. 9 is a graph of generator operating time versus carbon monoxide detection levels.

Referring to FIG. 9, a graph of generator run time versus sensed CO levels is illustrated. Graph 900 illustrates a current CO level curve 902 graphed against a calculated TWA curve 904. As shown, at point 906, the current CO level curve 902 is above a threshold above the TWA curve 904 such that the binary transient value will be set to one. At point 908, the current CO level curve 902 is below the TWA curve 904 such that the binary transient value will be set to zero. During window 910, the CO level curve 902 fluctuates rapidly such that it extends below and above the TWA curve 904.

Figure 10:
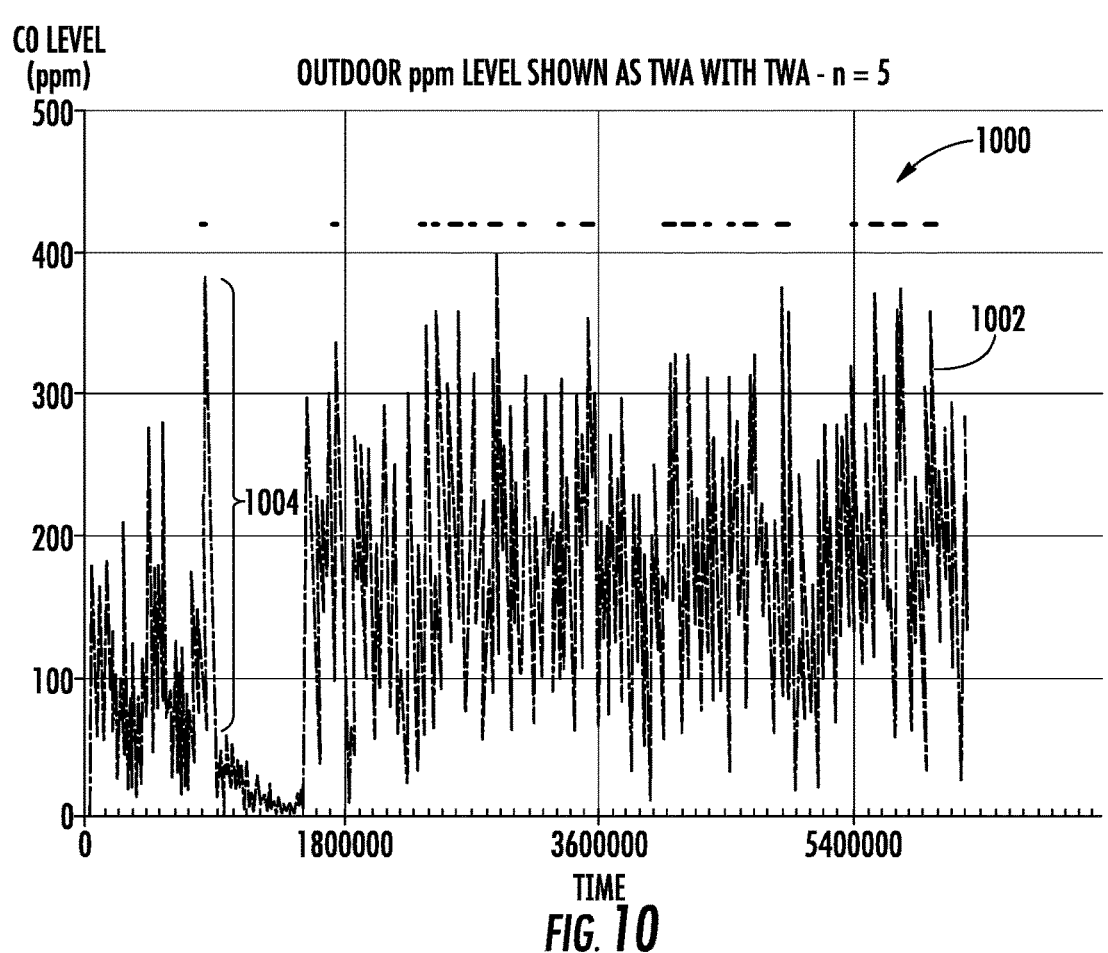
FIG. 10 is a graph of generator operating time versus carbon monoxide detection levels.

Referring to FIG. 10, a graph of generator run time versus sensed CO levels is illustrated. Graph 1000 illustrates a calculated TWA curve 1002. As shown, the TWA curve 1002 drops by a drop value 1004 within a short period of time. This CO drop-off behavior indicates that the generator may be in an open-air area where high fluctuations of CO levels may be read by the sensor 30. Accordingly, the drop-off behavior prompts the shutdown circuit 54 to switch the monitoring mode from a start-up mode to a continuous mode (e.g., method 600 in FIG. 6) at the point of the drop value 1004.

Figure 11:
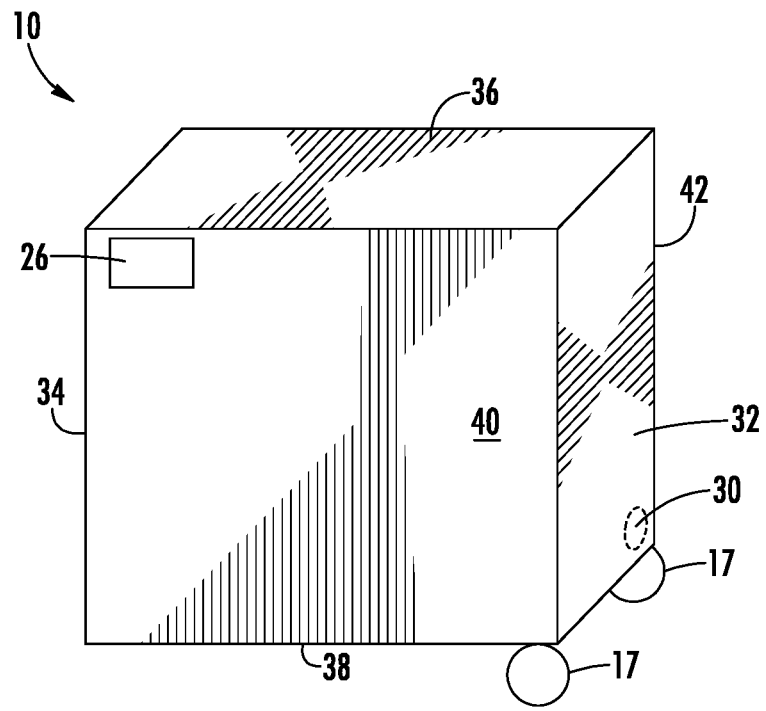
FIG. 11 is a schematic perspective view of the generator of FIG. 1.
Figure 12:
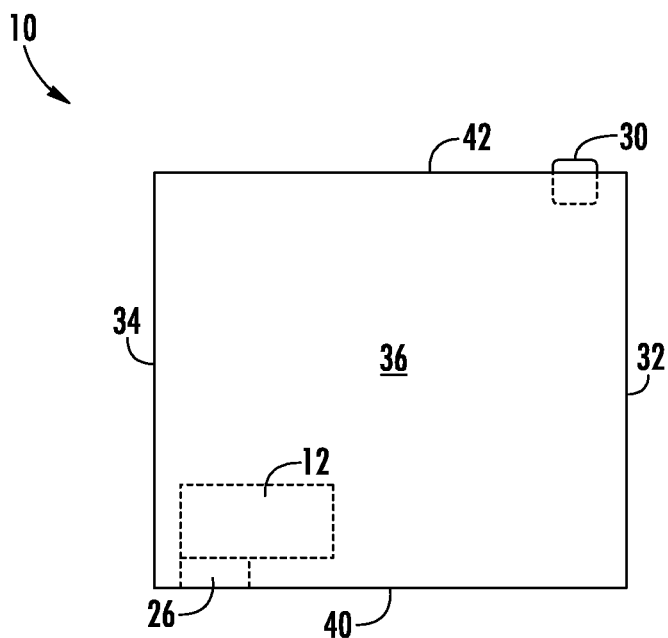
FIG. 12 is a schematic top view of the generator of FIG. 1.

Referring to FIGS. 11-12, the generator 10 includes a front 32, rear 34, top 36, bottom 38, left side 40, and right side 42. As shown in FIG. 11, the CO sensor 30 is positioned on the right side 42 near the front 32, while the exhaust outlet 26 is positioned on the left side 40 near the rear 34. In other embodiments, the CO sensor 30 may be positioned on another side of the generator 10 (e.g., front 32). While not limited to the exact positioning illustrated in FIGS. 11-12, the positioning of the CO sensor 30 is preferably selected such that exhaust gases exiting the exhaust outlet 26 are not blown back directly onto the CO sensor 30 in an environment with wind and/or air movement toward the exhaust outlet 26. Accordingly, when viewing the generator 10 from above as shown in FIG. 12, the CO sensor 30 is positioned on an opposite side of the generator 10 from the exhaust outlet 26 (e.g., diagonally opposite, directly opposite). In some embodiments, when viewed from above, the CO sensor 30 is positioned on an opposite side of the generator 10 from the engine 12 with the engine 12 located between the sensor 30 and the exhaust outlet 26. Positioning the sensor 30 as described helps to broaden the difference in variance seen in enclosed space versus open space running.

Additionally, the CO sensor 30 is positioned at an elevation lower than the exhaust outlet 26. Due to the relatively higher temperature of exhaust gases compared to atmospheric temperatures, the exhaust gases will rise upon exit from the exhaust outlet 26. Accordingly, positioning the CO sensor 30 at an elevation lower than the exhaust outlet 26 helps to prevent the continuous passing of exhaust gases over the CO sensor 30 during normal operation, while still allowing detection of elevated concentrations of CO due to accumulation over a period of time.

Figure 13:
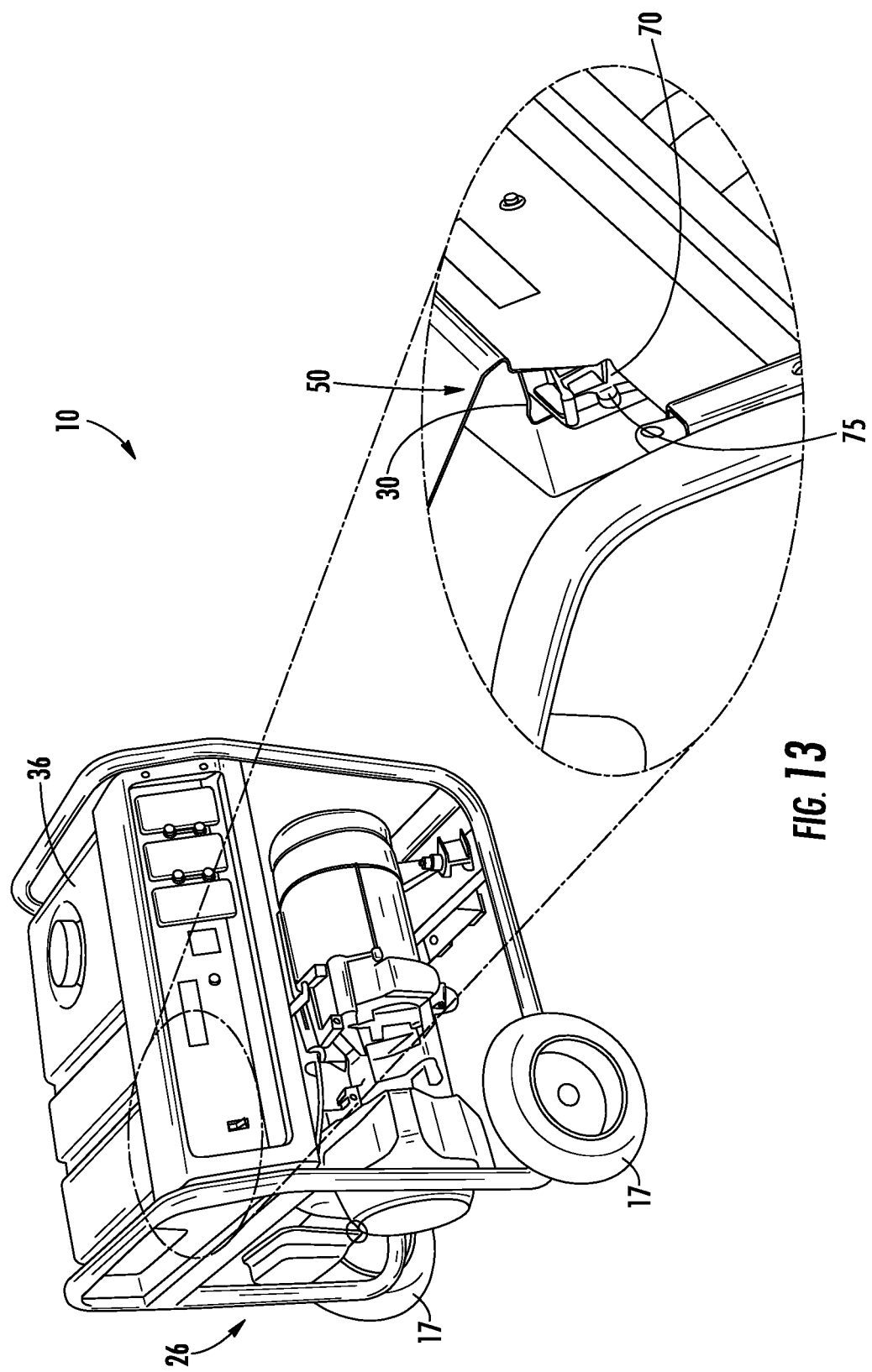
FIG. 13 is a perspective view with an enlarged detail of a portion of the generator of FIG. 1.

Referring to FIG. 13, another arrangement of the generator 10 and CO sensor 30 is shown, according to an exemplary embodiment. As shown, the CO sensor 30 includes the CO sensor controller 50, and CO notification 70 (e.g., alert light) as part of one CO sensor unit. The generator 10 includes the CO sensor 30 positioned (e.g., mounted using mounting feature 75) on the front 32 near the top 36 of the generator 10, while the exhaust outlet 26 is positioned on the rear 34 near the bottom 38. As described above, the positioning of the CO sensor 30 is preferably selected such that exhaust gases exiting the exhaust outlet 26 are not blown back directly onto the CO sensor 30 in an environment with wind and/or air movement toward the exhaust outlet 26.

The embodiments described herein have been described with reference to drawings. The drawings illustrate certain details of specific embodiments that implement the systems, methods and programs described herein. However, describing the embodiments with drawings should not be construed as imposing on the disclosure any limitations that may be present in the drawings.

It should be understood that no claim element herein is to be construed under the provisions of 35 U.S.C. § 112(f), unless the element is expressly recited using the phrase "means for."

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., integrated circuits (IC), discrete circuits, system on a chip (SOCs) circuits, etc.), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR, etc.), resistors, multiplexers, registers, capacitors, inductors, diodes, wiring, and so on).

The "circuit" may also include one or more processors communicably coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. Each processor may be implemented as one or more general-purpose processors, application specific integrated circuits (ASICs), field programmable gate arrays (FPGAs), digital signal processors (DSPs), or other suitable electronic data processing components structured to execute instructions provided by memory. The one or more processors may take the form of a single core processor, multi-core processor (e.g., a dual core processor, triple core processor, quad core processor, etc.), microprocessor, etc. In some embodiments, the one or more processors may be external to the apparatus, for example the one or more processors may be a remote processor (e.g., a cloud based processor). Alternatively or additionally, the one or more processors may be internal and/or local to the apparatus. In this regard, a given circuit or components thereof may be disposed locally (e.g., as part of a local server, a local computing system, etc.) or remotely (e.g., as part of a remote server such as a cloud based server). To that end, a "circuit" as described herein may include components that are distributed across one or more locations.

An exemplary system for implementing the overall system or portions of the embodiments might include a general purpose computing computers in the form of computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some embodiments, the non-volatile media may take the form of ROM, flash memory (e.g., flash memory such as NAND, 3D NAND, NOR, 3D NOR, etc.), EEPROM, MRAM, magnetic storage, hard discs, optical discs, etc. In other embodiments, the volatile storage media may take the form of RAM, TRAM, ZRAM, etc. Combinations of the above are also included within the scope of machine-readable media. In this regard, machine-executable instructions comprise, for example, instructions and data which cause a general purpose computer, special purpose computer, or special purpose processing machines to perform a certain function or group of functions. Each respective memory device may be operable to maintain or otherwise store information relating to the operations performed by one or more associated circuits, including processor instructions and related data (e.g., database components, object code components, script components, etc.), in accordance with the example embodiments described herein.

What is claimed is:

1. A generator comprising:
   an internal combustion engine; and
   a carbon monoxide (CO) sensor unit comprising:
      a CO sensor controller comprising:
         a CO sensing circuit configured to detect a level of CO; and
         a shutdown circuit configured to:

receive a detected level of CO;
calculate a trailing window average of the detected level of CO, the trailing window average comprising an average of the detected level of CO over at least two consecutive sampling loops;
determine whether to initiate a shutdown of the generator based on at least the calculated trailing window average and a predetermined trailing window average threshold; and
initiate the shutdown of the generator based on determining that the trailing window average exceeds the predetermined trailing window average threshold.

2. The generator of claim 1, wherein the shutdown circuit is further configured to:
calculate an array value based on the trailing window average and a currently detected level of CO.

3. The generator of claim 2, wherein the array value is calculated to be one if the currently detected level of CO exceeds a threshold above the trailing window average.

4. The generator of claim 3, wherein the array value is calculated to be zero if the currently detected level of CO is less than the threshold above the trailing window average.

5. The generator of claim 4, wherein the shutdown circuit is configured to initiate the shutdown of the generator based on determining that the array value exceeds a summed array value and the trailing window average exceeds a low trailing window average threshold;
wherein the low trailing average threshold is less than the predetermined trailing window average threshold;
wherein the summed array value comprises a sum of the array values within a pre-sized array of array values;
wherein the array value and the summed array value are reset to zero upon detection of the currently detected level of CO less than the threshold above the trailing window average.

6. The generator of claim 5, wherein the shutdown circuit is configured to initiate the shutdown of the generator only if a generator runtime is less than a generator runtime threshold.

7. The generator of claim 1, wherein the shutdown circuit monitors the trailing window average and the detected CO level based on at least a continuous monitoring mode and a start-up mode;
wherein the start-up mode is used when the generator runtime is less than a generator runtime threshold;
wherein the continuous mode is used when the generator runtime is equal to or greater than a generator runtime threshold.

8. The generator of claim 7, wherein the shutdown circuit switches from monitoring in the start-up mode to the continuous mode upon a drop between the calculated trailing window average value and a subsequent calculated trailing window average value being greater than a predetermined drop threshold.

9. The generator of claim 1, wherein the CO sensor controller further comprises:
an alert circuit configured to:
receive an indication from the shutdown circuit to trigger an alert on the generator; and
trigger the alert on the generator.

10. The generator of claim 9, further comprising an alert battery configured to provide power to the alert circuit and the alert.

11. The generator of claim 1, wherein the CO sensor unit further comprises a sensor power supply configured to receive power from the generator and provide power to the CO sensing unit.

12. The generator of claim 1, wherein the CO sensing circuit is coupled to the CO sensor unit and comprises a capacitor.

13. A carbon monoxide (CO) sensor system comprising:
a CO sensor; and
a CO sensor controller comprising:
a CO sensing circuit configured to detect a level of CO; and
a shutdown circuit configured to:
receive a detected level of CO;
calculate a trailing window average of the detected level of CO, the trailing window average comprising an average of the detected level of CO over at least two consecutive sampling loops;
determine whether to initiate a shutdown of an engine based on at least the calculated trailing window average and a predetermined trailing window average threshold; and
initiate the shutdown based on determining that the trailing window average exceeds the predetermined trailing window average threshold.

14. The system of claim 13, further comprising a CO sensor unit battery configured to provide power to the CO sensor and the CO sensor controller.

15. The system of claim 13, wherein the shutdown circuit is further configured to:
calculate an array value based on the trailing window average and a currently detected level of CO;
wherein the array value is calculated to be one if the currently detected level of CO exceeds a threshold above the trailing window average;
wherein the array value is calculated to be zero if the currently detected level of CO is less than the threshold above the trailing window average.

16. The system of claim 15, wherein the shutdown circuit is configured to initiate the shutdown based on determining that the array value exceeds a summed array value and the trailing window average exceeds a low trailing window average threshold;
wherein the low trailing average threshold is less than the predetermined trailing window average threshold;
wherein the summed array value comprises a sum of the array values within a pre-sized array of array values.

17. The system of claim 16, wherein the shutdown circuit is configured to initiate the shutdown only if an engine runtime is less than an engine runtime threshold.

18. The system of claim 13, wherein the shutdown circuit monitors the trailing window average and the detected CO level based on at least a continuous monitoring mode and a start-up mode;
wherein the start-up mode is used when an engine runtime is less than an engine runtime threshold;
wherein the continuous mode is used when the engine runtime is equal to or greater than the engine runtime threshold.

19. The system of claim 18, wherein the shutdown circuit switches from monitoring in the start-up mode to the continuous mode upon a drop between the calculated trailing window average value and a subsequent calculated trailing window average value being greater than a predetermined drop threshold.

20. The system of claim 13, wherein the CO sensor controller further comprises:

an alert circuit configured to:
   receive an indication from the shutdown circuit to trigger an alert; and
   trigger the alert.

21. The system of claim 20, further comprising an alert battery configured to provide power to the alert circuit and the alert.

22. The CO sensor system of claim 13, wherein the CO sensing circuit is coupled to the CO sensor unit and comprises a capacitor.

* * * * *